(12) United States Patent
Heidlas et al.

(10) Patent No.: US 6,680,284 B1
(45) Date of Patent: Jan. 20, 2004

(54) METHOD FOR PRODUCING POWDERY PARTICLE-REDUCED FORMULATIONS WITH THE AID OF COMPRESSED GASES

(75) Inventors: Jürgen Heidlas, Trostberg (DE); Martin Ober, Altenmarkt (DE); Johann Wiesmüller, Garching (DE)

(73) Assignee: Degussa AG, Trostberg (DE)

( * ) Notice: Subject to any disclaimer, the term of this patent is extended or adjusted under 35 U.S.C. 154(b) by 23 days.

(21) Appl. No.: 10/030,035

(22) PCT Filed: Jul. 13, 2000

(86) PCT No.: PCT/EP00/06709

§ 371 (c)(1),
(2), (4) Date: Jan. 3, 2002

(87) PCT Pub. No.: WO01/03671

PCT Pub. Date: Jan. 18, 2001

(30) Foreign Application Priority Data

Jul. 13, 1999 (DE) .......................... 199 32 648
Dec. 14, 1999 (DE) .......................... 199 60 167

(51) Int. Cl.⁷ .......................... A01N 25/12; A61K 9/16; B01J 3/00
(52) U.S. Cl. .......................... 504/367; 424/489; 424/499; 424/500; 424/501; 424/502; 514/959; 516/1; 516/114; 516/922; 516/928
(58) Field of Search .......................... 424/489, 499, 424/500, 501, 502; 514/951; 504/367; 516/1, 114, 922, 928

(56) References Cited

U.S. PATENT DOCUMENTS 5,399,597 A    3/1995   Mandel et al. .............. 523/342
5,854,311 A    12/1998  Richart .......................... 523/309
6,299,906 B1 * 10/2001  Bausch et al. ............... 424/489

FOREIGN PATENT DOCUMENTS

| DE | 40 41 563 | 6/1992 |
| EP | 0 542 314 | 5/1993 |
| EP | 0 677 332 | 10/1995 |
| WO | 99 52504 | 10/1991 |
| WO | 94 18264 | 8/1994 |

* cited by examiner

Primary Examiner—S. Mark Clardy
(74) Attorney, Agent, or Firm—Fulbright & Jaworski L.L.P.

(57) ABSTRACT

For the preparation of pulverulent particle-reduced formulations with the aid of compressed gases, the solid compound to be formulated, a poorly soluble and usually bioactive active compound, is homogeneously ground together with 10–99% by weight (based on the formulation) of a carrier material which is essentially soluble in the compressed gas mixture, in the presence of compressed gas or mixtures thereof in a stirred autoclave having a mechanical grinding device at process temperatures between 10 and 200° C. and at process pressures between 5 and 500 bar, and in a second process stage the compressed gas mixture, usually dimethyl ether, pure propane and/or carbon dioxide, is expanded by lowering the pressure and separated off from the homogenate, which can also be present as a melt. Finally, the pulverulent particle-reduced formulation is recovered from the homogenate obtained, with which significant improvements in the solubility properties and in particular in the bioavailability of originally poorly soluble and non-soluble compounds are to be achieved.

29 Claims, No Drawings

METHOD FOR PRODUCING POWDERY PARTICLE-REDUCED FORMULATIONS WITH THE AID OF COMPRESSED GASES

This application has been filed under 35 U.S.C 371 as the national stage of international application PCT/EP00/06709, filed Jul. 13, 2000.

The present invention describes a process for the preparation of pulverulent particle-reduced formulations with the aid of compressed gases.

A considerable number of substances such as active compounds, lacquers and additives often have only a very low solubility in water and in many organic solvents. The poor solubility of, especially, pharmaceutical active compounds is both a challenge to the pharmaceutical technologists, who attempt, using various formulation strategies, such as a reduction of the particle size and/or embedding in suitable additives, to achieve an improvement in solubility (Voigt, R., "Pharmazeutische Technologie" [Pharmaceutical Technology] 7th edition, Berlin: Ullstein Mosby, 1995), and for the active compound synthetic chemists, who attempt, by means of structural changes to the active compound molecules themselves, to improve their solubility without at the same time adversely affecting the active principles (Wermuth, C. G., "Preparation of Water-Soluble Compounds by Covalent Attachment of Solubilizing Moieties" in The Practice of Medicinal Chemistry, New York: Academic Press, pp. 755–776, 1996).

In pharmaceutical technology procedures, classical strategies for the reduction of the particle size and/or for the embedding of the active compound molecules in a solubility- or absorption-promoting matrix are predominant (Muranishi, S., Crit. Rev. Ther. Drug Carrier Syst. 7, 1–33 (1990)). Lipid vesicles, in particular liposomes, have also been proposed as active compound carriers (Lasic, D. D., J. Controlled Drug Release 48, 203–222 (1997)) which can bring about a specific improvement in the bioavailability of the active compounds after administration.

Many technological approaches, however, come up against their limits if a still acceptable bioavailability after administration is to be achieved for a poorly soluble active compound by a lowering of its particle size. To this end, a number of classical grinding techniques are admittedly available, such as, for example, with the aid of centrifugal force mills, pin beater mills, air-jet mills, ball mills, etc. (Voigt, R., "Pharmazeutische Technologie" [Pharmaceutical Technology] 7th edition, pp. 40, Berlin: Ullstein Mosby, 1995). These techniques, however, are often unsuitable for the realization of minimally achievable particle sizes and acceptable particle size distributions.

More recent technologies have therefore attempted to utilize the properties of compressed or supercritical gases for the preparation of micro- or nanoscale active compound particles (Howdle, S. et al. Proc. Int. Symp. Controlled Release Bioact. Mater. 25,972 (1998)), respectively, the following processes having gained acceptance:

1. The 'RESS process', in which the active compound is dissolved in the supercritical gas and then expanded through a fine nozzle and in the course of this "atomized",
2. The 'GASR process', in which the dissolved active compound is precipitated from a solution by the gas and under pressure, and finally
3. The PGSS process, in which, inter alia, coprecipitates between the respective active compound and a carrier, such as, for example, a polymer, are sprayed from a solution saturated with gas.

German laid-open applications DE-A-197 13 096, DE-A-197 58 157 and DE-A-198 29 396, for example, describe the homogeneous introduction of active substances having different solubility properties into various emulsifier matrices formed from solutions, achieving with the aid of compressed gases a solvent exchange in a column system, which leads to homogeneous formulations of originally poorly soluble active substances.

These more recent processes for particle production with the aid of compressed or supercritical gases, however, can only be employed if the active compounds can be brought into solution at least partially in the compressed gas itself or completely in a solvent. Unfortunately, in the case of many active compounds, coating agents such as, for example, lacquers, but also construction chemicals, such as, in particular, concrete additives, this is not the case or only the case to an insignificant extent, such that these procedures can either not be employed or can only be employed uneconomically in practice.

It was thus an object of the present invention to make available a process for the preparation of pulverulent particle-reduced formulations with the aid of compressed gases, with which poorly soluble or nonsoluble compounds can be formulated such that generally a significant improvement in the administrability and, in the case of bioactive substances, in particular a better bioavailability, are achieved.

"Particle-reduced" within the meaning of the present invention means that the proportion of particles having a diameter of >50 µm is lowered by >90% in relation to the starting material.

"Poorly soluble" within the meaning of the present invention means that at temperatures between 15 and 25° C., in particular at, for example, 20° C., for one part by mass of substance at least 100 parts by volume and preferably between 100 and 1000 parts by volume of solvent are needed (see also European Pharmacopeia, 3rd edition 1997, 1.3 monographs, p. 3).

This objective was achieved by a process in which a) the solid compound to be formulated is homogeneously ground at elevated process pressures in the presence of compressed gas together with 10 to 99% by weight of a carrier material based on the total weight of the particle-reduced formulation of compound and carrier material, the carrier material being essentially soluble in the compressed gas, and b) the compressed gas is then expanded by lowering the pressure, preferably to atmospheric pressure, and separated off from the homogenate, and the pulverulent particle-reduced formulation is recovered from the homogenate.

Surprisingly, it was possible to establish by means of the novel process that not only pulverulent particle-reduced formulations, but formulations are obtained which are completely homogeneous, i.e. formulations which quantitatively contain the compound to be formulated, that is the actual active compound, and which moreover no longer comprise particles which can be detected by light microscopy. This was not to be expected in this clarity.

Solid compounds to be formulated are understood within the meaning of the invention as meaning poorly soluble or nonsoluble compounds, in particular compounds which are poorly soluble or nonsoluble in a compressed gas in the absence of a carrier material. These are preferably bioactive compounds and in particular pharmaceutical and cosmetic active compounds; but also other poorly soluble substances whose solubility or bioavailability is to be improved can be employed. According to definition, pharmaceutical active compounds are substances which are suitable in medicinal therapy and diagnosis. In the present process, pharmaceutical compounds are preferably employed which can generally be administered topically, transdermally, perorally, parenterally and by inhalation, intravenously, intramuscularly, subcutaneously, intraperitoneally or intranasally. Cosmetic active compounds are as a rule understood as meaning substances which are applied to the skin.

Preferred solid compounds to be formulated within the meaning of the present invention, however, can also be poorly soluble or nonsoluble agrochemicals, such as, in particular, biocides (herbicides, fungicides, insecticides) or active compounds which are used as 'plant growth regulators' (PGR).

Lacquers or their constituents having poor solubility and certain concrete additives, i.e. construction chemicals, generally also come under the definition of the solid compound according to the invention.

Substances or substance mixtures in which the solid compound to be formulated can be embedded are typical carrier materials according to the invention. In this case, the proportion of carrier material can vary within wide ranges, the proportion, however, essentially being determined by the flowability of the formulation.

Proportions of the carrier material which are between 50 and 90% by weight in the formulation are to be preferred. In this case, synthetic and polymeric carriers are particularly suitable for the proposed preparation process, in particular polyethylene oxide block copolymers ("poloxamers"), polyethylene glycols, silicone derivatives such as methyl- or phenyl-substituted polysiloxanes having a differing degree of crosslinkage or gelatin and their derivatives. Particularly preferred substances are those having a surface-active action, such as natural and synthetically prepared phospholipids, especially glycerophospholipids ("lecithins"), partial glycerides such as mono- and/or diglycerides or carbohydrates and carbohydrate derivatives having a surface-active action, such as, for example, alkyl polyglycosides, sugar esters or sorbitan fatty acid esters, and their mixtures. An essential prerequisite for use of the carrier materials within the meaning of the invention is only to be defined in that these are either soluble in the respective compressed gas or a part of the gas dissolves in the carrier material itself. The latter is usually only manifested by the swelling of the carrier material under the corresponding conditions of the preparation process according to the invention. Highly suitable carrier materials are pharmaceutically acceptable substances or their mixtures which have already been described as absorption enhancers, especially in galenism.

The present process preferably proposes using, as compressed gases, propane or carbon dioxide or dimethyl ether (DME), but also any desired mixtures of propane and dimethyl ether, it also being possible to employ gas mixtures of propane and/or DME with up to 90% by weight, based on the gas mixture, of butane or carbon dioxide.

The grinding of the solid compound to be formulated with the carrier material in the presence of compressed gases, such as provided in the process according to the invention, can basically be carried out using all suitable grinding techniques which are known according to the prior art (Voigt, R., "Pharmazeutische Technologie" [Pharmaceutical Technology] 7th edition, pp. 40, Berlin: Ullstein Mosby, 1995). However, grinding in a stirred autoclave with a mechanical grinding device e.g. according to the principle of a ball mill, has proven particularly suitable, it being possible to carry out the grinding simply in a stirred autoclave running at high speed in the presence of grinding balls. The quantity, type and condition of the grinding balls and the speed and duration of the grinding process in this case in each case depend entirely on the properties of the solid compound to be ground.

As a result of the grinding process in the concentrated matrix of the carrier materials under pressure, the particulate, such as in particular crystalline, structures of the solid compound to be formulated are largely completely dissolved, and homogeneously embedded in the matrix, which, for example, can be readily demonstrated by means of light-microscopic observations of the result of grinding.

For specific process variants, in step a) grinding speeds have proven suitable for the homogeneous grinding which are between 500 and 4000 rpm, and in particular between 1000 and 2000 rpm. Grinding times of between 1 and 2 hours are particularly favorable; they can, however, also definitely be between 0.5 and 3 hours.

The conditions on the whole are chosen such that the carrier material can form a homogeneous phase, e.g. the compressed gas can be at least partially dissolved in the carrier material, i.e. under certain circumstances the carrier material can also only be present in the swollen state.

Suitable process pressures are preferably between 5 and 500 bar and particularly preferably between 40 and 120 bar; the process temperatures for the grinding in the compressed gas are preferably between 10 and 200° C. and particularly preferably between 50 and 120° C. in order to exclude thermal damage to the components.

In preferred process variants, conditions are chosen in which the carrier material, in particular the surface-active substance, is present in the compressed gas as a melt, i.e. in a 2-phase system: that is to say, in the lighter upper phase carrier material is then hardly dissolved, but it is found typically with a content of between usually 25 and 40% by weight of compressed gas in the heavier lower phase of the system. If glycerophospholipids are used as a carrier material, a melt is formed when using propane gas, for example, at pressures between 40 and 100 bar and temperatures between 40 and 100° C.

Optionally, in the present process small amounts of a suitable entraining agent, such as, in particular, short-chain $C_{1-4}$ alcohols, esters (e.g. ethyl acetate) or ketones (e.g. acetone) can be added in concentrations of up to 10% by weight, based on the reactor contents to be ground.

At this point, it may again be emphasized that the conditions only lead to the carrier material being dissolved in the manner described, but the solid compound is initially poorly soluble or not soluble in the system. The prerequisites of the process according to the invention of elevated pressure, elevated temperature and in particular the possibility of a highly concentrated form of the carrier material and, here in particular, of the surface-active compound in the form of a melt, are particularly suitable in order to convert the active compound to be ground into particles which are as small as possible or into solution by means of the grinding process, respectively.

It can be crucial for the success of the present process that not only the carrier material forms a melt under the respective process conditions, but that the entire autoclave contents are converted into a homogeneous melt by the grinding process; this variant is particularly taken into consideration by the invention.

It is likewise recommended that subsequent to the process step a) and additionally before the process step b) the stirrer speed is reduced to 50 to 200 and preferably to 100 rpm.

Using this measure, the homogenate has the possibility of collecting in the bottom region of the stirred autoclave without being able to demix in the course of this.

After the actual grinding process under pressure, it is possible according to the invention subsequently to free the ground product from the compressed gas in the second process step b). In terms of process technology, this takes place, in particular in the presence of a homogeneous melt, with the aid of a lowering of the pressure by means of an expansion nozzle, preferably towards atmospheric pressure, a pulverulent particle-reduced formulation product then being obtained.

It is to be taken into consideration that in many cases the expansion process itself on the whole no longer exerts a significant influence on the particle size of the compound to be formulated. The process according to the invention thus differs clearly from the principle of the RESS process, in which the particle size is determined exclusively by the nozzling process of the active compound dissolved in the supercritical gas.

The process according to the invention thus combines the following physical and physicochemical principles for particle reduction and simultaneous solubilization of poorly soluble or nonsoluble solid compounds (active compounds):

At elevated pressure in a compressed gas which optionally itself has certain solubility properties for the active compound, and using carrier materials, under the conditions of the process according to the invention a highly concentrated homogenate is obtained, preferably as a melt, the mechanical grinding preferably taking place according to the principle of a ball mill and, under certain circumstances, an additional reduction of the particle size being possible as a result of the expansion process of the compressed gas.

The following examples are intended to illustrate these advantages of the process according to the invention.

EXAMPLES

Example 1

20 g of aciclovir were mixed dry (powder mixture) with 80 g of oil-free soybean lecithin (not fractionated, obtained from Lucas Meyer, Hamburg) and introduced into a 400 ml stirred autoclave together with 70 ml of ceramic balls (diameter: 5 mm). The stirred autoclave was adjusted to a temperature of 60° C. and was then pressurized to 80 bar with propane gas, the lecithin being converted into a melt. The stirrer motor was then switched on and the grinding process was carried out at a stirrer speed of 1000 rpm, keeping the pressure and temperature constant over a period of 2 hours, it being clearly possible to discern the grinding noises of the balls.

After these 2 hours, the stirrer speed was reduced to about 100 rpm in order to give the melt the opportunity to sediment in the bottom region of the autoclave. The melt prepared in this way was then expanded from 80 bar to atmospheric pressure via a pressure valve at the bottom of the autoclave, whereby a spontaneous evaporation of the propane gas was achieved and a pulverulent product was obtained. A content determination showed that the aciclovir was contained quantitatively in the formulation.

In a microscopic investigation, it was found that the defined particles of the starting material (particle size spectrum between 50 and 250 µm) were dissolved and absorbed in the amorphous matrix of the soybean lecithin. A microscopic determination of the particle size of the acyclovir was no longer possible.

Example 2

5 g of crystalline β-carotene (synthetic material, obtained from BASF, Ludwigshafen) were mixed dry (powder mixture) with 95 g of oil-free lyso-soybean lecithin (Emulfluid®, obtained from Lucas Meyer, Hamburg) and introduced into a 400 ml stirred autoclave together with 70 ml of ceramic balls (diameter: 5 mm). The stirred autoclave was adjusted to a temperature of 80° C. and pressurized to 100 bar with a mixture consisting of 90% by weight of propane gas and 10% by weight of DME, the lyso-lecithin being converted into a melt. The grinding process was then carried out at a stirrer speed of 3000 rpm and keeping the pressure and temperature constant over a period of 0.5 hours.

The stirrer speed was then reduced to about 100 rpm in order to give the melt the opportunity to settle in the bottom region of the autoclave. The melt prepared in this way was then expanded from 100 bar to atmospheric pressure via a pressure valve at the bottom of the autoclave, whereby a spontaneous evaporation of the gas mixture was achieved and a pulverulent, strongly red-colored product was obtained.

In the microscopic investigation, it was found that the crystalline structures of the starting material have been almost completely dissolved and incorporated into the amorphous matrix of the lyso-soybean lecithin. In an analysis of the isomeric composition, it was found that during the formulation process only a slight isomerization (<5%) of the all-trans-β-carotene had taken place.

Example 3

15 g of β-sitosterol were mixed dry (powder mixture) with 85 g of alkyl polyglycoside (APG, Tego Care CG 90, obtained from Th. Goldschmidt, Essen) and introduced into a 400 ml stirred autoclave together with 70 ml of ceramic balls (diameter: 5 mm). The stirred autoclave was adjusted to a temperature of 120° C. and pressurized with a mixture consisting of 80% by weight of propane gas and 20% by weight of DME, the APG being converted into a melt. The grinding process was then carried out at a stirrer speed of 1000 rpm and keeping the pressure and temperature constant over a period of 2.5 hours.

The stirrer speed was then reduced to about 100 rpm in order to give the melt the opportunity to settle in the bottom region of the autoclave. The melt prepared in this way was then expanded from 80 bar to atmospheric pressure by means of a pressure valve at the bottom of the autoclave, whereby a spontaneous evaporation of the gas mixture was achieved and a pulverulent, homogeneously white product was obtained.

The microscopic investigation showed that the particle structures of the starting material were almost completely dissolved. The product showed a strongly improved dispersibility in lipophilic and hydrophilic media.

What is claimed is:

1. A process for the preparation of pulverulent particle-reduced formulations with the aid of compressed gases, wherein
    (a) the solid compound to be formulated is homogeneously ground at elevated process pressures in the presence of compressed gas together with 10 to 99% by weight of a carrier material based on the total weight of the particle-reduced formulation of compound and carrier material, the carrier material being essentially soluble in the compressed gas, and
    (b) the compressed gas is then expanded by lowering the pressure and separated off from the homogenate, and the pulverulent particle-reduced formulation is recovered from the homogenate.

2. The process as claimed in claim 1, wherein the solid compound to be formulated is poorly soluble or nonsoluble in the compressed gas in the absence of the carrier material.

3. The process as claimed in claim 1 wherein in process step a) 50 to 90% by weight, of carrier material are added based on the particle-reduced formulation.

4. The process as claimed in claim 1, wherein the grinding step is conducted in a stirred autoclave having an integrated ball mill.

5. The process as claimed in claim 1, wherein, in process step a), up to 10% by weight, based on the contents of an entraining agent to be ground, are added.

6. The process as claimed in claim 1, wherein, in process step a), the pressure is adjusted to 5 to 500 bar.

7. The process as claimed in claim 1, wherein in process step a), the temperature is adjusted to 10 to 200° C.

8. The process as claimed in claim 1, wherein in process step a), the contents of the autoclave are ground to give a homogeneous melt.

9. The process as claimed in claim 1, wherein, at the end of the process step a), the stirrer speed is reduced to 50 to 200 rpm.

10. The process as claimed in claim 1, wherein, in process step b), the lowering of the pressure is carried out by means of an expansion nozzle.

11. The process as claimed in claim 1, wherein, in process step a), the pressure is adjusted to 40 to 120 bar.

12. The process as claimed in claim 1, wherein in process step a), the temperature is adjusted to 50 to 120° C.

13. The process as claimed in claim 1, wherein the solid compound to be formulated is a bioactive.

14. The process of claim 13, wherein the bioactive compound is a pharmaceutically or cosmetically active compound.

15. The process of claim 13, wherein said bioactive compound is suitable for at least one of peroral, parenteral, inhalational, intravenous, intramuscular, subcutaneous, intraperitoneal, intranasal, topical and transdermal administration.

16. The process as claimed in claim 1, wherein the solid compound to be formulated is an agrochemical.

17. The process of claim 16, wherein said agrochemical is selected from the group consisting of a biocide and a plant growth regulator.

18. The process as claimed in claim 1, wherein the solid compound to be formulated is a construction chemical.

19. The process of claim 18 wherein said construction chemical is selected from the group consisting of a lacquer and a concrete additive.

20. The process as claimed in claim 1, wherein the carrier material is a surface-active substance.

21. The process of claim 20, wherein said carrier material is selected from the group consisting of a phospholipid, a partial glyceride, a carbohydrate derivative, a polymers, a polyethylene glycol, a silicone derivative, and a gelatin.

22. The process of claim 20, wherein said carrier material is selected from the group consisting of a glycerophospholipid, a monoglyceride, a diglyceride, a carbohydrate derivative selected from the group consisting of an alkyl polyglycoside, a sugar ester, and a sorbitan fatty acid ester; a synthetic polymer, a natural polymer, a methyl-substituted polysiloxane, and a phenyl-substituted polysiloxane.

23. The process of claim 22, wherein said carrier material is a polyethylene oxide block copolymers ("poloxamer").

24. The process as claimed in claim 1, wherein said compressed gas is at least one gas selected from the group consisting of propane, dimethyl ether, carbon dioxide, and butane.

25. The process of claim 24, wherein said compressed gas is a mixture of propane or dimethyl ether of up to 90% by weight of the gas mixture and at least one of butane and carbon dioxide.

26. The process as claimed in claim 1, wherein in process step a), the homogeneous grinding is carried out at a stirrer speed of 500 to 4000 rpm.

27. The process of claim 26, wherein the stirrer speed is from 1000 to 2000 rpm.

28. The process as claimed in claim 1, wherein, in process step a), the homogeneous grinding is carried out over a period of 0.5 to 3 hours.

29. The process of claim 28, wherein the entraining agent is selected from the group consisting of a $C_{1-4}$-alcohol, a $C_{1-4}$ ester and a $C_{1-4}$ ketone.

* * * * *